(12) United States Patent
Marks et al.

(10) Patent No.: US 6,416,789 B1
(45) Date of Patent: Jul. 9, 2002

(54) SYNERGISTIC COMBINATION OF FUNGICIDES TO PROTECT WOOD AND WOOD-BASED PRODUCTS FROM FUNGAL DECAY, MOLD AND MILDEW DAMAGE

(75) Inventors: Brian Marks, Oakmont; Alan S. Ross, Pittsburgh; Hans A. Ward, Wexford, all of PA (US)

(73) Assignee: Kop-Coat, Inc., Pittsburgh, PA (US)

( * ) Notice: Subject to any disclaimer, the term of this patent is extended or adjusted under 35 U.S.C. 154(b) by 0 days.

(21) Appl. No.: 09/755,729

(22) Filed: Jan. 5, 2001

(51) Int. Cl.[7] ............... A01N 59/14; A01N 59/16; A01N 47/12; A01N 47/10; A01N 33/24
(52) U.S. Cl. ............... 424/641; 424/617; 424/657; 424/658; 424/659; 424/660; 424/DIG. 11; 514/64; 514/478; 514/479; 514/480; 514/481; 514/483; 514/484; 514/485; 514/486; 514/487; 514/488; 514/489; 514/644; 514/788; 514/975
(58) Field of Search .............. 514/64, 478, 479–481, 514/484–489, 644, 788, 975, 483; 424/657–660, DIG. 11, 617

(56) References Cited

U.S. PATENT DOCUMENTS

| 4,552,885 A | 11/1985 | Gabriele |
| 4,950,685 A | 8/1990 | Ward |
| 5,389,300 A | 2/1995 | Schmitt |
| 5,846,305 A | 12/1998 | Payzant |
| 5,985,301 A | 11/1999 | Nakamura |
| 5,990,043 A | 11/1999 | Kugler |
| RE36,798 E | 8/2000 | Williams |

*Primary Examiner*—John Pak
(74) *Attorney, Agent, or Firm*—Debra Z. Anderson; Eckert Seamans Cherin & Mellott, LLC

(57) ABSTRACT

A wood treatment material having a synergistic combination of fungicides including boron-containing compounds, organo-iodine compounds and amine-oxides is provided. This combination is shown to be especially effective in providing resistance to decay, mold and mildew when wood is treated with this combination. Also provided is wood treated by this combination, and a method of treatment for composite wood.

39 Claims, No Drawings

SYNERGISTIC COMBINATION OF FUNGICIDES TO PROTECT WOOD AND WOOD-BASED PRODUCTS FROM FUNGAL DECAY, MOLD AND MILDEW DAMAGE

BACKGROUND OF THE INVENTION

1. Field of the Invention

This invention relates to a synergistic combination of three fungicides, boron-containing compounds, organo-iodine compounds and amine oxides, which when used in combination, give a synergistic result in providing improved resistance to mold, mildew and fungal decay on wood treated with this combination. Wood treated with this combination, and a method of treating wood, are also included in the present invention.

2. Description of the Prior Art

Wood is one of the best structural materials for the construction of buildings because of its strength, ease of processing and relatively low cost. However, wood and wood-based materials, including cellulosic composites and plastic-wood composites, are susceptible to both structural and cosmetic damage from fungal decay, mold and mildew.

Currently, a variety of fungicides including boron compounds are available to protect wood and wood composites from decay. For example, it is known to use zinc borate to protect cellulosic composites, including particleboard, hardboard and oriented strandboard, from fungal decay, as described in U.S. Pat. Nos. 4,879,083; 5,763,338; and 5,972,266. Zinc borate is usually applied as a powder or a liquid suspension to wood chips or strands, prior to their fabrication into panels. However, zinc borate is not a very cost-effective wood preservative, and does not provide good protection against mold, mildew and staining fungi at typical use levels.

It is also known to use iodopropargyl derivatives such as 3-iodo-2-propynyl-n-butyl carbamate (IPBC) for protection against fungi which cause structural and cosmetic damage to wood. However, while effective, this compound used alone is expensive and requires larger amounts to achieve the desired end result.

U.S. Pat. No. 5,389,300 provides a composition for protecting sawn timber against wood discoloring fungi, containing a phenol fungicide and an organo-iodine fungicide such as IPBC. Other fungicides, insecticides, or active ingredients, including boron compounds, can be added to the composition.

U.S. Pat. No. 5,846,305 discloses a wood preservative composition comprising a copper compound, an amine solvent and a boron compound. The preferred boron compound is sold by U.S. Borax, Inc. under the tradename "TIM-BOR."

U.S. Pat. No. Re 36,798 provides a preservative composition for treatment of wood and other cellulosic materials, comprising a biocidal metal compound and a fungicidal compound containing a triazole group. Compositions of this invention may contain other organic fungicides, insecticides, or bacteriocides, including boron in any form, such as boric acid, boron, or boron esters.

U.S. Pat. No. 4,950,685 relates to a wood preservative composition which provides stain resistance to wood. The composition comprises a synergistic combination of a quaternary ammonium compound and IPBC.

U.S. Pat. No. 5,990,043 relates to an anti-fouling composition which includes a carrier, a binder, and an effective amount of at least one insecticide, which can be a carbamate. Synergistic effects are observed when combinations of two or more of the numerous insecticides listed are used in combination.

It is desired, therefore, to develop a wood treatment substance capable of protecting wood against fungal decay, mold and mildew in an economical manner.

SUMMARY OF THE INVENTION

The present invention fulfills the above need by providing an unusually effective and economical wood treatment that protects wood and wood products against fungal decay, mold and mildew. The present invention provides a unique combination of three classes of fungicides, specifically boron-containing fungicides, organo-iodine fungicides and amine oxide fungicides, which in combination provide a more complete resistance to decay, in a more economical manner, than use of any of these compounds individually. A method of treating wood, in particular composite wood materials, with the synergistic combination is included in the present invention, as is the wood treated by this combination.

It is an object of the invention therefore, to provide a combination of fungicides to resist decay in wood treated with such substances, in an economical manner.

It is a further object of the present invention to provide an economical wood treatment which can resist decay using boron-containing fungicides in combination with organo-iodine and amine oxide compounds.

It is an additional object of the present invention to provide a method of treating wood using this synergistic combination of fungicides.

It is an additional object of the present invention to provide wood treated with a synergistic combination of fungicides.

These and other objects of the invention will become apparent from the following description and appended claims.

DETAILED DESCRIPTION OF PREFERRED EMBODIMENTS

Accordingly, the present invention provides a wood treatment material comprising a synergistic combination of a boron-containing fungicide, an organo-iodine compound and an amine oxide compound. As used herein, the term "wood treatment material" refers to this synergistic combination of fungicides, which may be used with other additives such as resins or solvents, and which is applied to wood by a variety of methods including, but not limited to, spraying, dipping, pressure treating, addition during formation of engineered wood, and other methods used to apply such substances to wood and are known to those skilled in the art.

As used herein, the term "boron-containing fungicide" includes fungicides containing at least one boron compound selected from the group including boron, alkali metal salts of boron, alkaline earth metal salts of boron, metal salts of boron, oxides of boron, boric acid, boric acid esters and salts of these. It is thought that in respect to the metal salts of boron the active part of the compound is the boron, rather than metallic, portion.

As used herein, the term "organo-iodine compounds" refers to a category of organo-iodine compounds known to have biocidal activity and to provide protection against fungi when applied to wood and other materials.

Examples of organo-iodine compounds which may be used in the present invention include, but are not limited to, iodopropargyl derivatives including compounds derived from propargyl or iodopropargyl alcohols such as the esters, ethers, acetals, carbamates and carbonates and the iodopropargyl derivatives of pyrimidines, thiazolinones, tetrazoles, triazinones, sulfamides, benzothiazoles, ammonium salts, carboxamides, hydroxamates, and ureas. This class of compounds has the general formula:

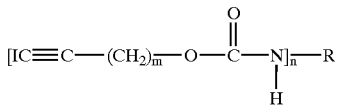

wherein R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and from substituted and unsubstituted cycloalkyl and cycloalkenyl groups of 3 to 10 carbon atoms, and m and n are independently integers from 1 to 3, i.e., m and n are not necessarily the same.

Preferred are formulations where m is 1 and n is 1 having the following formula:

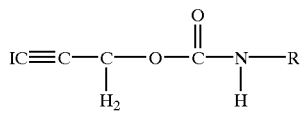

Suitable R substituents include alkyls such as methyl, ethyl, propyl, n-butyl, t-butyl, pentyl, hexyl, heptyl, octyl, nonyl, decyl, dodecyl, octadecyl, cycloalkyls such as cyclohexyl, aryls, alkaryls and aralkyls such as phenyl, benzyl, tolyl, cumyl, halogenated alkyls and aryls, such as chlorobutryl and chlorophenyl, and alkoxy aryls such as ethoxyphenyl and the like.

Compounds of this formula include iodopropargyl carbamates such as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof. Most preferred is 3-iodo-2-propynyl butyl carbamate (IPBC).

As used herein, the term "amine oxide compounds" refers to those compounds which are formed as reaction products in the reaction of tertiary amines and hydrogen peroxides and are represented by the general formula:

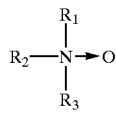

where $R_1$, $R_2$ and $R_3$ are independent and can be straight or branched, saturated or unsaturated carbon chains from 1 to 20 carbons in length.

Preferred amine oxides are alkyl dimethyl amine oxides such as decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide and octyl dimethyl amine oxide. Most preferred is N-alkyl-N, N-dimethylamine oxide (ADO).

As used herein, the term "wood" includes a variety of wood and wood-based materials, including but not limited to logs and other types of dried lumber, green lumber, fiberboard, strand board, laminated veneer lumber, cellulosic composites, plastic wood composites and other types of wood, wood composites and engineered wood formed from wood flakes, chips, strands, veneers and adhesives.

In a method of creating the wood product, the fungicides can be applied on the surface of the wood, as in spraying or dipping the wood in a suspension containing all three fungicides. Typically, the organo-iodine compound and the amine-oxide compound are pre-mixed with solvents in a ratio of about 4 parts organo-iodine compound, 27 parts amine-oxide compound and 6 parts solvent (the remaining 63 parts consists of inactive material due to the manner of packaging active ingredients for sale). Any organic solvent can be used, but polar organic solvents are preferred as they will provide better solubilization of the organo-iodine compound. Most preferred are solvents such as dimethyl sulfoxide and dipropylene glycol.

Other constituents of the solution may include wax emulsion or other water repellant, solvents and/or water. The fungicides can also be applied to the wood with pressure treatment that is commonly used on solid or engineered wood. A third method, particularly for plywood, is to treat the wood chips, flakes or strands with the fungicide combination in powder or liquid form prior to formation of the composite wood boards. Wood may be treated by more than one of these methods, and as used herein the term "treatment" refers to any one of these or other methods known to those skilled in art and which are used to apply these or similar substances to wood.

The wood treated by the composition of the present invention will have, on a weight to weight percent basis, a boron-containing compound present in the wood in an amount of about 0.1 wt. % to about 5 wt. %, more preferably about 0.2 wt. % to about 0.6 wt. %. The organo-iodine compound will be present in the wood in an amount of between about 10 ppm to about 1,000 ppm, more preferably between about 20 ppm and about 100 ppm. The amine-oxide compound will be present in the wood in an amount of between about 80 ppm to about 9,000 ppm, more preferably between about 200 ppm and about 600 ppm. All weight percent or part-per-million values are based on the total weight of the wood, either before or after high pressure treatment and excluding the weight of resins, waxes or other materials used in processing.

In the third method referred to above, the fungicides are combined with wood flakes, chips or strands, an adhesive such as a phenolic or isocyanate resin or other similar resin known to those skilled in the art, and a water repellant and fabricated into a wood composite board. This last step may be accomplished in a heated high-pressure press. These severe processing conditions often result in reduced performance of additives such as fungicides. Unexpectedly, the performance of a boron compound in combination with an organo-iodine compound and an amine-oxide compound was not reduced, but was actually improved. This combination of fungicides has proven to be unusually effective in providing resistance to decay, mold and mildew.

EXAMPLE 1

An oriented strand board wood panel having the dimensions 12-in. by 12 in. by ⅜ in. was made as follows: 800 grams of wood strand flakes were placed in a tumbler with 3.70 grams of powdered zinc borate (US Borax Borogaurd) and 24 grams of powdered phenolic resin (Georgia-Pacific Resins). The mixture was tumbled for 15 minutes to ensure complete dispersion. 19.2 grams of wax emulsion (Hercules Paracol 802N), 0.05 grams of IPBC (Troy Polyphase P100) and 0.315 grams of amine oxide (Lonza Barlox 12 (30% amine oxide)) were mixed together in a spray pump container. The wax and fungicide combination was then sprayed onto the wood flakes tumbling in the tumbler and tumbled for 15 minutes after completion of spraying.

Platens were preheated to 450° F. (hardboard requires 350° F.). Flakes were removed from the tumbler and formed into a panel using a forming box. When the platens reached the proper temperature the formed panel was placed in the press and a pressure of 650 psi (600 psi for hardboard) applied. The pressure was maintained until the panel reached a core temperature of 250° F., at which time a 10 to 30 second degassing period was allowed. The panel was then removed from the press. The panel produced by this method contained 0.466% zinc borate, 390 ppm amine oxide and 60 ppm IPBC, based on the weight of the wood excluding resin and wax.

Similar panels having varying amounts of each fungicide and different combinations of fungicides (as described in Table 1) were also fabricated by the above method and used in the bioassay test described below.

Evaluation of fungicide performance was conducted using an accelerated laboratory bioassay test. This test was carried out as follows:

A test chamber consisting of an aluminum pan with an inside dimension of 26 cm×20 cm×6 cm was prepared by covering the pan with aluminum foil and autoclaving at 121° C. for 45 minutes. Malt agar was prepared by adding, in an Erlenmeyer flask, 15 grams of Bacto-Agar and 20 grams of Malt Extract with 965 ml of distilled water. The solution was heated until the agar was clear, and the agar was then autoclaved at 121° C. for 45 minutes.

In a sterile environment, the malt agar was added to the bottom of the test chamber. A sufficient amount of agar was needed to maintain fungal growth and to avoid the desiccation of the chamber. The above pan size requires about 750 ml of agar.

Next, wood samples were added to the test chamber. Samples were first surface sterilized with an alcohol lamp to avoid Deuteromycete contamination in the decay portion of the test. One drop of homogenized culture inoculum was added around each sample, and at least one drop for every 10 mm of sample length was used. The following groupings of organisms were used in the inoculum (these groups were applied to separate samples):

Group 1 Basidiomycete Blend—*Serpula lacrimans, Gloeophyllum trabeum, Lentius lepideus, Poria placenta, Corious versicolor.*

Group 2 Deuteromycete Blend—*Acremonium strictum, Chaetomium globosum, Graphium rubrum, Trichoderma sp., Trichoderma viride, Aspergillus sp., Aspergillus niger, Paecilomyces varioti, Gliocladium sp., Cephaloascus fragrans, Aureobasidium pullalans, Diplodia gossypina, Chlorociboria aeruginascens, Cladosporium cladosporiodes, Penicillium purpurogenum, Alternaria alternata.*

The test chamber was incubated at 32° C. (90° F.) and 90% relative humidity.

Basidiomycete Evaluation: after fifteen and thirty days of incubation, fungal growth on the surface of the samples was evaluated. Evaluation was made visually using a scale from −10 to 10, with minus ten (−10) indicating an inhibitory zone of 10 mm around the sample. Zero (0) indicates no inhibitory zone, but no infection of the sample. Ten (10) indicates a sample covered with mycelium.

Evaluations were converted from the scale (−10 to 10) to express percentage of wood surface area protected using the following equation:

[(Visual Evaluation)−10]×(−10)=Percentage of Wood Surface Area Protected

After conversion, one way analysis of variance and Student's t-Tests were used to test for treatment differences at a determined error rate of probability (i.e., 0.05).

Deuteromycete Evaluation: after five and fifteen days of incubation, fungal growth on the surface of the samples was evaluated. Evaluations were made visually using a scale from −10 to 10. Minus ten (−10) indicates an inhibitory zone of 10 mm around the sample. Zero (0) indicates no inhibitory zone, but no infection of the sample. Ten (10) indicates a sample covered with mycelium.

Evaluations were converted from the scale (−10 to 10) to express percentage of wood surface area protected using the following equation:

[(Visual Evaluation)−10]×(−10)=Percentage of Wood Surface Area Protected

After conversion, one way analysis of variance and Student's t-Tests were used to test for treatment differences at a determined error rate of probability (i.e., 0.05).

Results are presented in Table 1.

TABLE 1

| Sample Number | Amount of Fungicide | Deuteromycete (% Protection) | Basidiomycete (% Protection) |
|---|---|---|---|
| 14 | 0 | 8% | 38% |
| 15 | 4130 ppm ZB | 23 | 42 |
| 16 | 8260 ppm ZB | 69 | 92 |
| 27 | 605 ppm ADO | 14 | 34 |
| 31 | 605 ppm IPBC | 82 | 98 |
| 28 | 526 ppm ADO + 79 ppm IPBC | 59 | 46 |
| 25 | 392 ppm ADO + 58 ppm IPBC + 4130 ppm ZB | 92 | 90 |
| 17 | 392 ppm ADO + 58 ppm IPBC + 4130 ppm ZB | 96 | 98 |

From Table 1 it can be seen that the highest levels of surface protection using the least amounts of ingredients are obtained with the combination of 392 ppm ADO, 58 ppm IPBC and 4130 ppm zinc borate (Sample 17). This level of performance is equivalent to 8260 ppm of zinc borate alone or 605 ppm of IPBC alone; however, it is more cost effective than either. Thus the unique combination of three classes of fungicides of the present invention provide a more complete resistance to decay in a more economical manner, than use of any of these compounds individually.

EXAMPLE 2

Oriented strand board wood panels were made and evaluated as in Example 1. The results are presented in Table 2.

TABLE 2

| Sample Number | Amount of Fungicide | Deuteromycete (% Protection) | Basidiomycete (% Protection) |
|---|---|---|---|
| 51 | 109 ppm ADO + 16 ppm IPBC + 4130 ppm ZB | 19% | 16% |
| 52 | 196 ppm ADO + 29 ppm IPBC + 4130 ppm ZB | 94 | 80 |
| 53 | 287 ppm ADO + 33 ppm IPBC + 4130 ppm ZB | 99 | 93 |
| 54 | 392 ppm ADO + 58 ppm IPBC + 4130 ppm ZB | 99 | 86 |

TABLE 2-continued

| Sample Number | Amount of Fungicide | Deuteromycete (% Protection) | Basidiomycete (% Protection) |
|---|---|---|---|
| 56 | 109 ppm ADO + 16 ppm IPBC + 2100 ppm ZB | 99 | 80 |
| 57 | 196 ppm ADO + 29 ppm IPBC + 2100 ppm ZB | 99 | 74 |
| 58 | 287 ppm ADO + 33 ppm IPBC + 2100 ppm ZB | 99 | 96 |
| 59 | 392 ppm ADO + 58 ppm IPBC + 2100 ppm ZB | 99 | 99 |
| 66 | 109 ppm ADO + 16 ppm IPBC | 32 | 7 |
| 67 | 218 ppm ADO + 32 ppm IPBC | 75 | 32 |
| 68 | 392 ppm ADO + 58 ppm IPBC | 55 | 60 |
| 49 | 2100 ppm ZB | 5 | 1 |
| 50 | 4130 ppm ZB | 7 | 4 |
| 55 | Control | 12 | 3 |

From Table 2, it can be seen that the highest levels of protection can be obtained using the least amounts of ingredients with the combination of 392 ppm ADO, 55 ppm IPBC and 2,100 ppm zinc borate (Sample 59). For an unknown reason Sample 51 showed a lower than expected level of protection.

It will be appreciated that the present invention provides a wood treatment material having a synergistic combination of fungicides including boron-containing compounds, organo-iodine compounds and amine-oxides which is especially effective in providing resistance to decay, mold and mildew when wood is treated with this combination. While particular embodiments of this invention have been described above for purposes of illustration, it will be evident to those skilled in the art that numerous variations of the details of the present invention may be made without departing from the invention as defined in the appended claims.

We claim:

1. A fungicidal wood treatment material comprising a synergistic combination of a boron-containing fungicide, an organo-iodine compound represented by the formula:

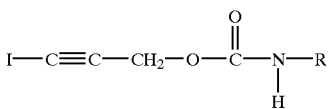

wherein R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and substituted and unsubstituted cycloalkyl and cycloalkenyl groups of 3 to 10 carbon atoms, and an amine-oxide compound represented by the formula:

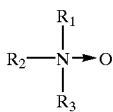

where $R_1$, $R_2$ and $R_3$ are independent and can be straight or branched, saturated or unsaturated carbon chains from 1 to 20 carbons in length.

2. The wood treatment material of claim 1, wherein the boron-containing fungicide is selected from the group consisting of alkali metal salts of boron, alkaline earth metal salts of boron, metal salts of boron, oxides of boron, boric acid, boric acid esters and salts thereof.

3. The wood treatment material of claim 1, wherein the organo-iodine compound is selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

4. The wood treatment material of claim 1, wherein the amine-oxide compound is selected from the group consisting of decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide, octyl dimethyl amine oxide, N-alkyl-N, N-dimethylamine oxide and mixtures thereof.

5. The wood treatment material of claim 1, wherein the boron fungicide is present in an amount of about 0.1 to 0.6 wt. %, the organo-iodine compound is present in an amount of about 5 to 100 ppm, and the amine-oxide compound is present in an amount of about 50 to 600 ppm, based on the weight of the wood excluding resins or waxes.

6. The wood treatment material of claim 5, wherein the boron-containing fungicide is zinc borate, the organo-iodine compound is 3-iodo-2-propynyl-n-butylcarbamate and the amine-oxide compound is N-alkyl-N, N-dimethylamine oxide.

7. The wood treatment material of claim 2, wherein the boron-containing fungicide is zinc borate.

8. The wood treatment material of claim 2, wherein the boron-containing fungicide is calcium borate.

9. The wood treatment material of claim 2, wherein the boron-containing fungicide is sodium borate.

10. The wood treatment material of claim 2, wherein the boron-containing fungicide is boric acid.

11. The wood treatment material of claim 3, wherein the organo-iodine compound is 3-iodo-2-propynyl-n-butylcarbamate.

12. The wood treatment material of claim 4, wherein the amine-oxide compound is N-alkyl-N, N-dimethylamine oxide.

13. A fungicide treated wood comprising wood treated with a synergistic combination of a boron-containing fungicide, an organo-iodine compound of the formula:

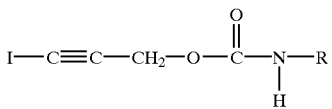

wherein R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and from substituted and unsubstituted cycloalkyl and cycloalkenyl groups of 3 to 10 carbon atoms, and an amine-oxide compound of the formula:

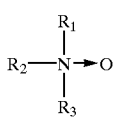

where $R_1$, $R_2$ and $R_3$ are independent and can be straight or branched, saturated or unsaturated carbon chains from 1 to 20 carbons in length.

14. The fungicide treated wood of claim 13, wherein the boron-containing fungicide is selected from the group consisting of alkali metal salts of boron, alkaline earth metal salts of boron, metal salts of boron, oxides of boron, boric acid, boric acid esters and salts thereof.

15. The fungicide treated wood of claim 13, wherein the organo-iodine compound is selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

16. The fungicide treated wood of claim 13, wherein the amine-oxide compound is selected from the group consisting of decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide, octyl dimethyl amine oxide, N-alkyl-N, N-dimethylamine oxide and mixtures thereof.

17. The fungicide treated wood of claim 13, wherein the boron-containing fungicide is present in an amount of about 0.1 to 0.6 wt. %, the organo-iodine compound is present in an amount of about 5 to 100 ppm, and the amine-oxide compound is present in an amount of about 50 to 600 ppm, based on the weight of the wood excluding resins or waxes.

18. The fungicide treated wood of claim 17, wherein the boron-containing fungicide is zinc borate, the organo-iodine compound is 3-iodo-2-propynyl-n-butylcarbamate and the amine-oxide is N-alkyl-N, N-dimethylamine oxide.

19. The fungicide treated wood of claim 14, wherein the boron-containing fungicide is zinc borate.

20. The fungicide treated wood of claim 14, wherein the boron-containing fungicide is calcium borate.

21. The fungicide treated wood of claim 14, wherein the boron-containing fungicide is sodium borate.

22. The fungicide treated wood of claim 14, wherein the boron-containing fungicide is boric acid.

23. The fungicide treated wood of claim 15, wherein the organo-iodine compound is 3-iodo-2-propynyl-n-butylcarbamate.

24. The fungicide treated wood of claim 16, wherein the amine-oxide compound is N-alkyl-N, N-dimethylamine oxide.

25. The fungicide treated wood of claim 13, wherein the wood is engineered wood.

26. A method of treating wood comprising treating wood with a synergistic combination of a boron-containing fungicide, an organo-iodine compound of the formula:

$$I-C\equiv C-CH_2-O-\underset{H}{\overset{O}{\underset{\|}{C}}}-N-R$$

wherein R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and from substituted and unsubstituted cycloalkyl and cycloalkenyl groups of 3 to 10 carbon atoms, and an amine-oxide compound represented by the formula:

$$R_2-\underset{R_3}{\overset{R_1}{\underset{|}{N}}}\rightarrow O$$

where $R_1$, $R_2$ and $R_3$ are independent and can be straight or branched, saturated or unsaturated carbon chains from 1 to 20 carbons in length.

27. The method of claim 26, including employing said method on wood components of an engineered wood product, prior to formation of said engineered wood product.

28. The method of claim 26, wherein the boron-containing fungicide is selected from the group consisting of alkali metal salts of boron, alkaline earth metal salts of boron, metal salts of boron, oxides of boron, boric acid, boric acid esters and salts thereof.

29. The method of claim 26, wherein the organo-iodine compound is selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

30. The method of claim 26, wherein the wherein the amine-oxide compound is selected from the group consisting of decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide, octyl dimethyl amine oxide, N-alkyl-N, N-dimethylamine oxide and mixtures thereof.

31. The method of claim 26, wherein the boron-containing fungicide is present in an amount of about 0.1 to 0.6 wt. %, the organo-iodine compound is present in an amount of about 5 to 100 ppm, and the amine-oxide compound is present in an amount of about 50 to 600 ppm, based on the total weight of the wood.

32. The method of claim 31, wherein the boron-containing fungicide is zinc borate, the organo-iodine compound is 3-iodo-2-propynyl-n-butylcarbamate and the amine-oxide is N-alkyl-N, N-dimethylamine oxide.

33. The method of claim 28, wherein the boron-containing fungicide is zinc borate.

34. The method of claim 28, wherein the boron-containing fungicide is calcium borate.

35. The method of claim 28, wherein the boron-containing fungicide is sodium borate.

36. The method of claim 28, wherein the boron-containing compound is boric acid.

37. The method of claim 29, wherein the organo-iodine compound is 3-iodo-2-propynyl-n-butylcarbamate.

38. The method of claim 30, wherein the amine-oxide compound is N-alkyl-N, N-dimethylamine oxide.

39. A fungicidal wood treatment material comprising a synergistic combination of a boron-containing fungicide, an organo-iodine compound represented by the formula:

$$[I-C\equiv C-(CH_2)_{\overline{m}}-O-\underset{H}{\overset{O}{\underset{\|}{C}}}-N]_{\overline{n}}-R$$

wherein R is selected from the group consisting of hydrogen, substituted and unsubstituted alkyl groups having from 1 to 20 carbon atoms, substituted and unsubstituted aryl, alkylaryl, and aralkyl groups having from 6 to 20 carbon atoms and substituted and unsubstituted cycloalkyl and cycloalkenyl groups of 3 to 10 carbon atoms, and n and m are independently integers from 1 to 3;
and an amine-oxide compound represented by the formula:
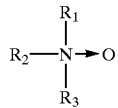
where $R_1$, $R_2$ and $R_3$ are independent and can be straight or branched, saturated or unsaturated carbon chains from 1 to 20 carbons in length.
* * * * *